United States Patent
Rogers et al.

(10) Patent No.: US 9,462,994 B2
(45) Date of Patent: Oct. 11, 2016

(54) BIOACOUSTIC SENSOR WITH ACTIVE NOISE CORRECTION

(71) Applicant: 3M INNOVATIVE PROPERTIES COMPANY, St. Paul, MN (US)

(72) Inventors: Daniel J. Rogers, Grant, MN (US); Justin Tungjunyatham, Roseville, MN (US); Christopher J. Roed, Minneapolis, MN (US)

( * ) Notice: Subject to any disclaimer, the term of this patent is extended or adjusted under 35 U.S.C. 154(b) by 10 days.

(21) Appl. No.: 14/400,082

(22) PCT Filed: May 9, 2013

(86) PCT No.: PCT/US2013/040335
§ 371 (c)(1),
(2) Date: Nov. 10, 2014

(87) PCT Pub. No.: WO2013/170018
PCT Pub. Date: Nov. 14, 2013

(65) Prior Publication Data
US 2015/0119758 A1    Apr. 30, 2015

Related U.S. Application Data

(60) Provisional application No. 61/645,887, filed on May 11, 2012.

(51) Int. Cl.
| A61B 7/04 | (2006.01) |
| H04R 17/02 | (2006.01) |
| A61B 5/00 | (2006.01) |

(Continued)

(52) U.S. Cl.
CPC ............... *A61B 7/04* (2013.01); *A61B 5/7203* (2013.01); *A61B 7/026* (2013.01); *H04R 17/025* (2013.01); *H04R 1/46* (2013.01); *H04R 2217/01* (2013.01); *H04R 2410/05* (2013.01)

(58) Field of Classification Search
CPC .. H04R 1/46; H04R 2420/07; H04R 17/025; H04R 1/10; H04R 3/00; H04R 1/2811; H04R 2430/03; H04R 29/001
USPC ........... 381/67, 1, 107, 117, 17, 384, 56, 60, 381/62, 71.6, 72, 75, 77
See application file for complete search history.

(56) References Cited

U.S. PATENT DOCUMENTS

| 3,995,124 A | 11/1976 | Gabr |
| 4,127,749 A | 11/1978 | Atoji |
| 4,156,800 A | 5/1979 | Sear |

(Continued)

FOREIGN PATENT DOCUMENTS

| CA | 2122108 | 10/1994 |
| EP | 0814456 | 12/1997 |

(Continued)

OTHER PUBLICATIONS

International Search Report for PCT International Application No. PCT/US2013/040335, mailed on Aug. 23, 2013, 4pgs.

*Primary Examiner* — Akelaw Teshale

(57) ABSTRACT

A bioacoustic sensor assembly is described including a transducer generating an acoustic signal and an actuator configured to deform a portion of the transducer to increase a signal-to-noise ratio of the acoustic signal. The disclosure also provides methods and systems for reducing the impact of noise vibrations at the transducer.

14 Claims, 5 Drawing Sheets

(51) Int. Cl.
*A61B 7/02* (2006.01)
*H04R 1/46* (2006.01)

(56) References Cited

U.S. PATENT DOCUMENTS

| | | | |
|---|---|---|---|
| 4,442,323 A | 4/1984 | Yoshida | |
| 5,182,771 A | 1/1993 | Munich | |
| 5,492,129 A | 2/1996 | Greenberger | |
| 5,494,043 A | 2/1996 | O'Sullivan | |
| 5,497,426 A | 3/1996 | Jay | |
| 5,539,831 A | 7/1996 | Harley | |
| 5,602,924 A | 2/1997 | Durand | |
| 5,699,437 A | 12/1997 | Finn | |
| 5,812,678 A | 9/1998 | Scalise | |
| 5,812,679 A | 9/1998 | Killion | |
| 5,917,919 A * | 6/1999 | Rosenthal | G10K 11/1786 381/71.11 |
| 6,028,942 A | 2/2000 | Greenberger | |
| 6,134,331 A | 10/2000 | Baekgaard | |
| 6,178,246 B1 | 1/2001 | Bebesel | |
| 6,520,918 B1 | 2/2003 | Stergiopoulos | |
| 6,654,467 B1 | 11/2003 | York | |
| 7,006,638 B1 | 2/2006 | Baekgaard | |
| 7,130,429 B1 | 10/2006 | Dalgaard | |
| 7,317,801 B1 * | 1/2008 | Amir | G10K 11/1782 379/406.05 |
| 7,593,534 B2 * | 9/2009 | Andersen | A61B 7/04 181/131 |
| 7,991,165 B2 | 8/2011 | Kassal | |
| 8,024,974 B2 | 9/2011 | Bharti | |
| 2003/0002685 A1 | 1/2003 | Werblud | |
| 2004/0037429 A1 | 2/2004 | Candioty | |
| 2004/0037430 A1 * | 2/2004 | Kim | G10K 11/178 381/71.8 |
| 2006/0153394 A1 | 7/2006 | Beasley | |
| 2007/0003072 A1 | 1/2007 | Ward | |
| 2007/0041274 A1 | 2/2007 | Shertukde | |
| 2007/0113649 A1 * | 5/2007 | Bharti | A61B 5/4818 73/431 |
| 2008/0232604 A1 | 9/2008 | Dufresne | |
| 2009/0034746 A1 | 2/2009 | Nozaki | |
| 2011/0125060 A1 | 5/2011 | Telfort | |
| 2011/0213271 A1 | 9/2011 | Telfort | |
| 2013/0150754 A1 | 6/2013 | Rogers | |

FOREIGN PATENT DOCUMENTS

| | | |
|---|---|---|
| GB | 1565860 | 4/1980 |
| JP | 57034679 | 2/1982 |
| WO | WO 94-23420 | 10/1994 |

* cited by examiner

BIOACOUSTIC SENSOR WITH ACTIVE NOISE CORRECTION

BACKGROUND

A variety of bioacoustic sensors have been developed to detect sounds produced by the body, such as heart and lung sounds. Known devices range from mechanical devices, such as stethoscopes, to various electronic devices, which can typically include microphones and transducers.

Although many electronic bioacoustic sensors are available on the market, they have yet to gain universal acceptance by the physicians and other medical practitioners. Possible reasons for non-acceptance of electronic bioacoustic sensors include the production of noise or artifacts that disturb the clinician during patient evaluation, as well as limitations associated with amplification and reproduction of certain biological sounds of interest. In general, bioacoustic sensors, including electronic stethoscopes, are preferentially designed to detect acoustic vibrations emanating from the body. In practice, however the acoustic vibrations detected include both bodily acoustic sounds indicative of physiological parameters (e.g., breathing sounds indicative of respiratory rate, heart sounds, etc.) and acoustic vibrations from environmental noise (sometimes referred to as ambient noise) emanating from one or more noise sources. For example, the acoustic noise may include noise from an external noise source, such as electronics (e.g., computers, medical equipment, motors, pumps, fans, alarms, or other electronics, etc.), noise from other people such as visiting family members and medical personnel in the vicinity of the patient, vehicle noise (e.g., in a helicopter), etc. In some circumstances, the acoustic noise includes sounds coming from the patient that are not indicative of measured physiological parameters. Such sounds may include patient speech, coughing, etc. As a result, the bioacoustic sensor, typically a transducer, will produce a signal indicative of all detected acoustic vibrations. Each signal will therefore include a physiological sound component representative of the physiological parameter of interest and an acoustic noise component representative of environmental and/or other noise.

The signal-to-noise ratio of bioacoustic sensor signals is generally reduced due to the presence of the acoustic noise, regardless of the source. In some circumstances, a reduced signal-to-noise ratio can make it difficult to distinguish the physiological sound components of the signal from the noise components to provide accurate measurements. This problem is particularly exacerbated in some emergency environments, such as in-flight helicopters and ambulances, where the noise detected by the sensor can be orders of magnitude greater than the body sounds of interest.

Various techniques are known in the art to reduce the presence and effect of noise in the acoustic signal. In a typical approach, as exemplified by US Publication No. 2011/1213271 (Telfort et al.), systems are designed to collect signals from more than one acoustic sensing element, and then combine (e.g., summing, subtracting, averaging, etc.) the respective outputs from those sensing elements in a manner that tends to reinforce the physiological components of the signals while tending to cancel or reduce the noise components of the signals.

SUMMARY

While known noise reduction techniques and processes may be helpful in certain circumstances, the reliance on downstream processing can be insufficient when the physiologic sounds of interest are effectively masked by high levels of noise. The bioacoustic sensor systems of the present disclosure utilize a feedback loop to cancel or reduce the effect of ambient noise impinging on a transducer at the transducer itself. The bioacoustic sensor systems of the present disclosure incorporate an actuator directly physically coupled to at least a portion surface of a transducer configured to generate a signal in response to deformation by impinging acoustic vibrations. One or more reference sensors, in addition to the transducer, can be provided to preferentially sense ambient noise. Output signals from both the transducer and the reference sensor can be communicated to a signal processing circuit that contains a vibration control module. The vibration control module determines the noise by reference to a least one of the output signals, generates a control signal, and communicates the control signal to excite the actuator. The actuator then physically deforms the transducer to counteract the effect of unwanted vibrations (i.e., noise), based at least partially on one or more components of the control signal. Certain bioacoustic sensor systems of the present disclosure can advantageously utilize adaptive filtering, so that both periodic and sporadic noise may be accounted for in the control signal. Accordingly, the noise is cancelled or substantially reduced at the transducer itself, so that the signal generated by the transducer has an improved signal-to-noise ratio prior to any downstream signal processing.

Since the signal generated by the transducer has a higher signal-to-noise ratio, the bioacoustic sensor systems of the present disclosure are particularly well suited for use in emergency or combat medicine, where a patient's condition must be assessed and evaluated under considerable ambient noise. Exemplary conditions include accidents, natural disasters, and combat situations where care must be administered amidst extreme conditions, such as patient transport aboard ambulances, which may generate substantial operating noise. The bioacoustic sensor systems of the present disclosure may be particularly well suited for use in military aircraft, where the level of ambient noise may be orders of magnitude greater than the sounds of interest emanating from a patient.

In one aspect, the present disclosure provides a system for acquiring bioacoustic signals. The system can include a transducer assembly including a transducer configured to sense a manifestation of acoustic energy and an actuator mechanically/physically coupled to a first major surface of the transducer, wherein the transducer is configured to generate an acoustic signal; a reference sensor configured to generate a reference signal; a processor coupled to the reference sensor and the transducer; and noise vibration control circuitry coupled to the reference sensor and the actuator, the noise vibration control circuitry configured to generate an anti-noise signal based at least partially on a component of the reference signal, the anti-noise signal operable to cause the actuator to deform at least a portion of the transducer, wherein the deformation of the transducer increases a signal-to-noise ratio of the acoustic signal.

In another aspect, the present disclosure provides a bioacoustic sensor comprising a housing configured for handheld manipulation; a transducer assembly supported by the housing that senses auscultation signals, the transducer assembly comprising a transducer having a first major surface and an actuator physically coupled to the transducer; a headset coupled to the housing and configured to deliver audio corresponding to the auscultation signals through earpieces on the headset; a reference sensor configured to generate a reference signal; a processor disposed in the housing and configured to convert the auscultation signals to first digital signals representative of the auscultation signals; and noise vibration control circuitry coupled to the reference sensor and the actuator, the noise vibration control circuitry configured to generate an anti-noise signal, wherein the anti-noise signal is based at least partially on a component of the reference signal and is operable to cause the actuator to deform at least a portion of the transducer, and wherein the deformation of the transducer increases a signal-to-noise ratio of the acoustic signal.

In yet another aspect, the present disclosure provides a method of increasing the signal-to-noise ratio of a signal generated by an acoustic sensor. The method can include providing a transducer assembly and a reference sensor remote from the assembly, wherein the transducer assembly comprises a transducer and an actuator coupled to a first major surface of the transducer; providing noise vibration control circuitry coupled to the reference sensor and the actuator; generating an acoustic signal from the transducer and a reference signal from the reference sensor; providing at least the reference signal to the noise vibration control circuitry; generating an anti-noise signal based at least partially on a component of the reference signal; providing the anti-noise signal to the actuator; and deforming at least a portion of the transducer via the actuator.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a," "an," "the," "at least one," and "one or more" are used interchangeably. Thus, for example, a system comprising "a" reference sensor can be interpreted as a system comprising "one or more" reference sensors.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

BRIEF DESCRIPTION OF THE DRAWINGS

The invention will be further described with reference to the drawings, wherein corresponding reference characters indicate corresponding parts throughout the several views, and wherein.

Layers in certain depicted embodiments are for illustrative purposes only and are not intended to absolutely define the thickness, relative or otherwise, or the location of any component. While the above-identified figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention.

DETAILED DESCRIPTION OF ILLUSTRATIVE EMBODIMENTS

The present disclosure is directed to an improved bioacoustic sensor capable of being utilized in areas having high to extremely high ambient noise levels while still effectively conveying clear and accurate sounds emanating from within the body of a patient. In this regard, the bioacoustic sensor systems of the present disclosure are particularly well suited for use in the field, particularly with respect to emergency or combat medicine, where a patient's condition must be assessed and evaluated under considerable ambient noise. Exemplary conditions include accidents, natural disasters, and combat situations where care must be administered amidst extreme conditions, such as patient transport aboard ambulances and aircraft, which may generate substantial operating noise. The bioacoustic sensor systems of the present disclosure may be particularly well suited for use in military aircraft, where the level of ambient noise may be orders of magnitude greater than the sounds of interest emanating from a patient.

The bioacoustic sensor systems of the present disclosure utilize a feedback loop to cancel or reduce the effect of ambient noise impinging on a transducer. For example, a bioacoustic sensor system may incorporate an actuator physically coupled to at least a portion surface of a transducer. One or more reference sensors, in addition to the transducer, can be provided to preferentially sense noise. Output signals from both the transducer and the reference signal can be communicated to a signal processing circuit that contains a vibration control module. The vibration control module determines the noise by reference to a least one of the output signals, generates a control signal, and communicates the control signal to excite the actuator. The actuator then physically deforms the transducer to counteract the effect of unwanted noise vibrations, based at least partially on one or more components of the control signal.

Figure 1:
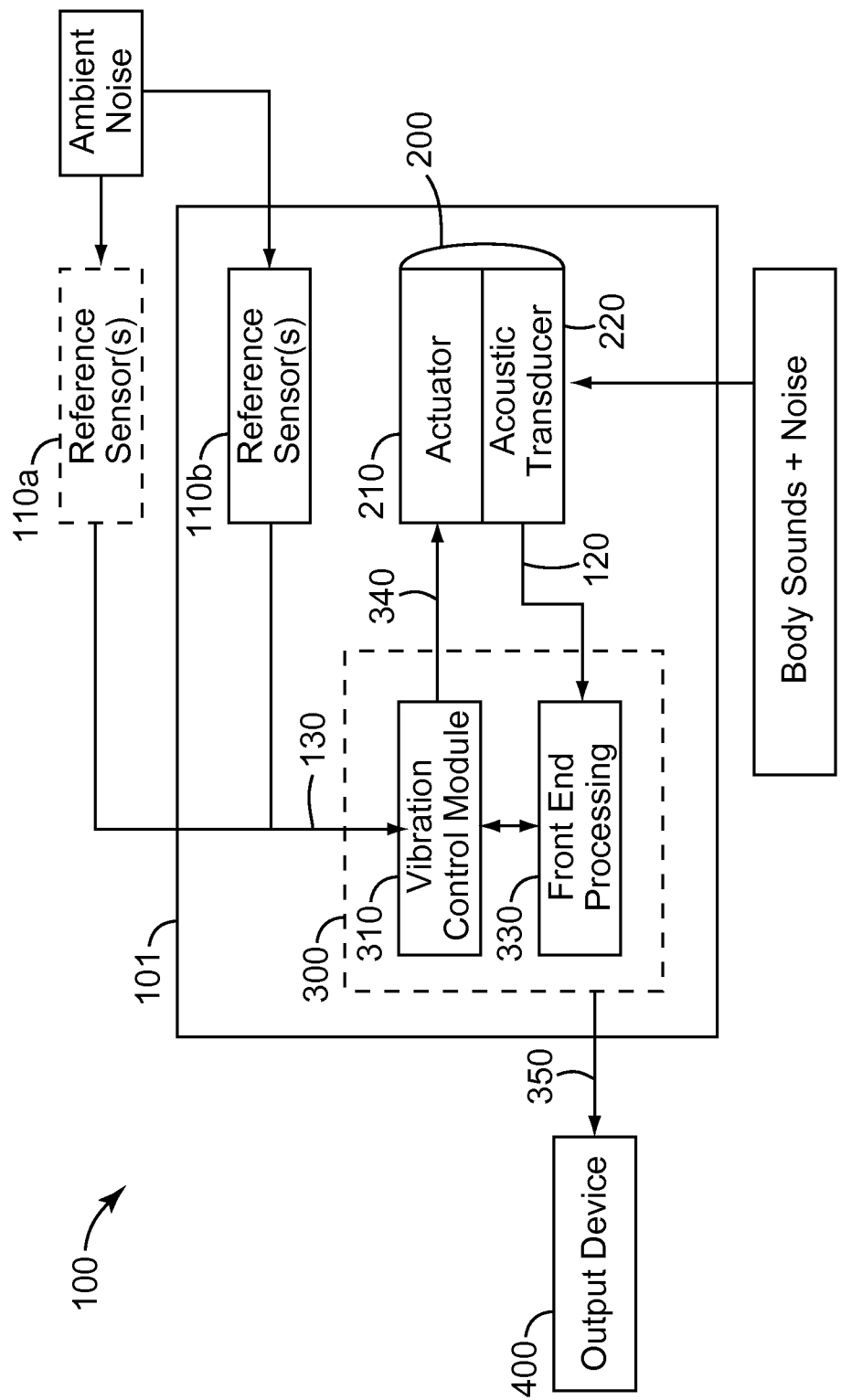
FIG. 1 depicts a block diagram of a bioacoustic sensor system according to an embodiment of the present disclosure.
Figure 2:
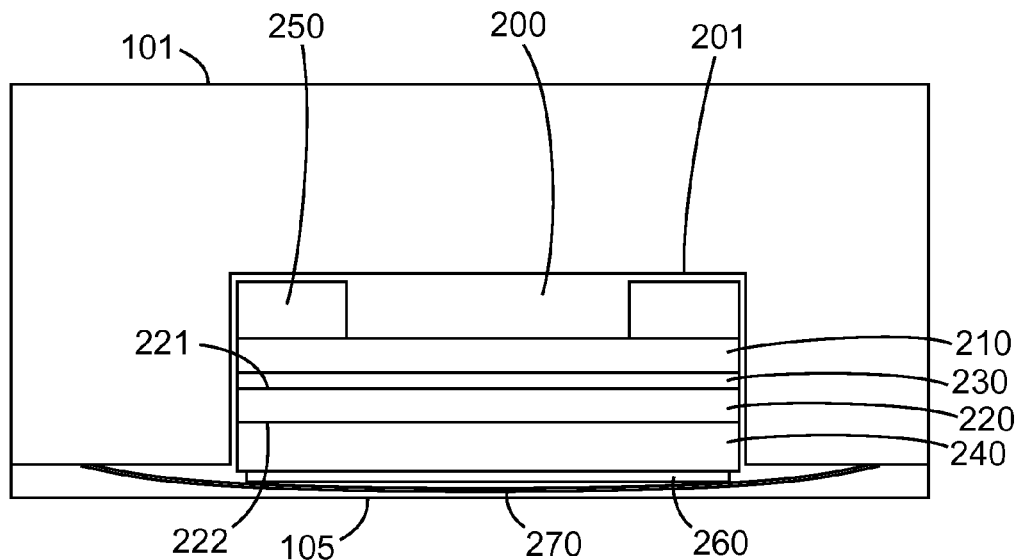
FIG. 2 is a diagram of a transducer assembly according to an implementation of the present disclosure.
Figure 3:
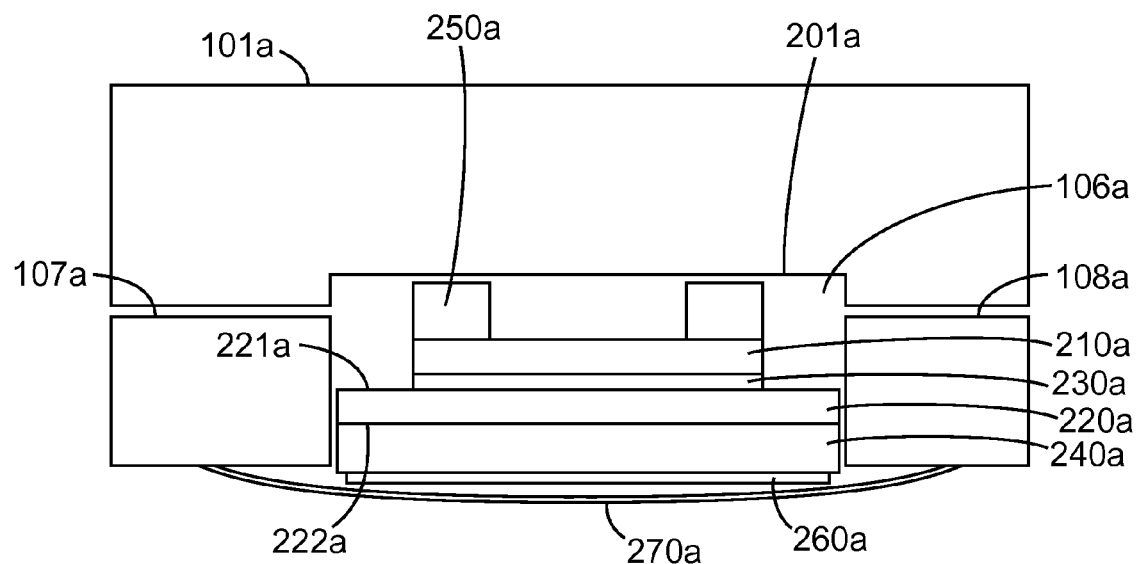
FIG. 3 is a diagram of another transducer assembly according to an implementation of the present disclosure.
Figure 4:
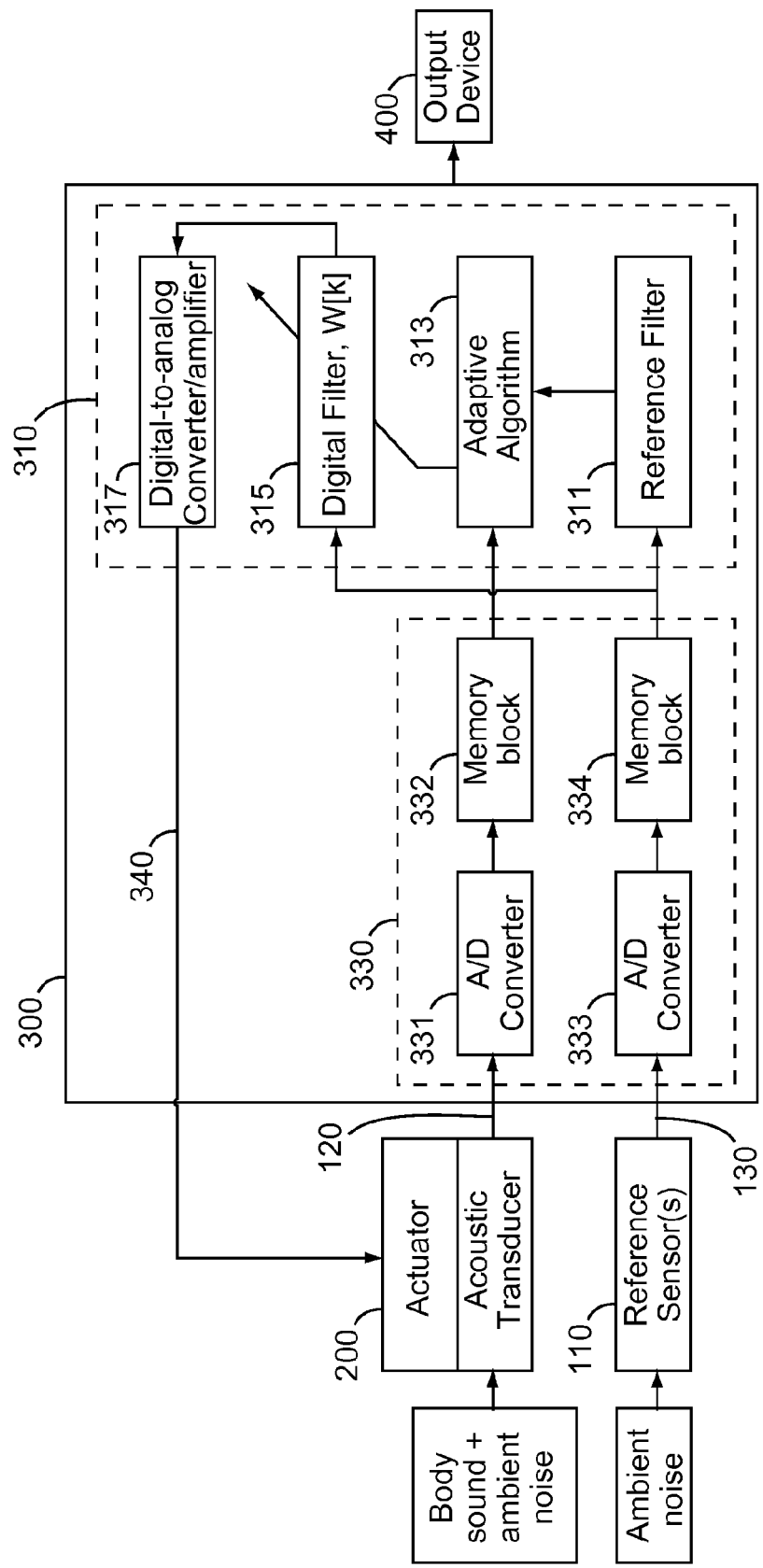
FIG. 4 is a functional block diagram of a bioacoustic sensor system including a vibration control module, according to an implementation of the present disclosure.
Figure 5:
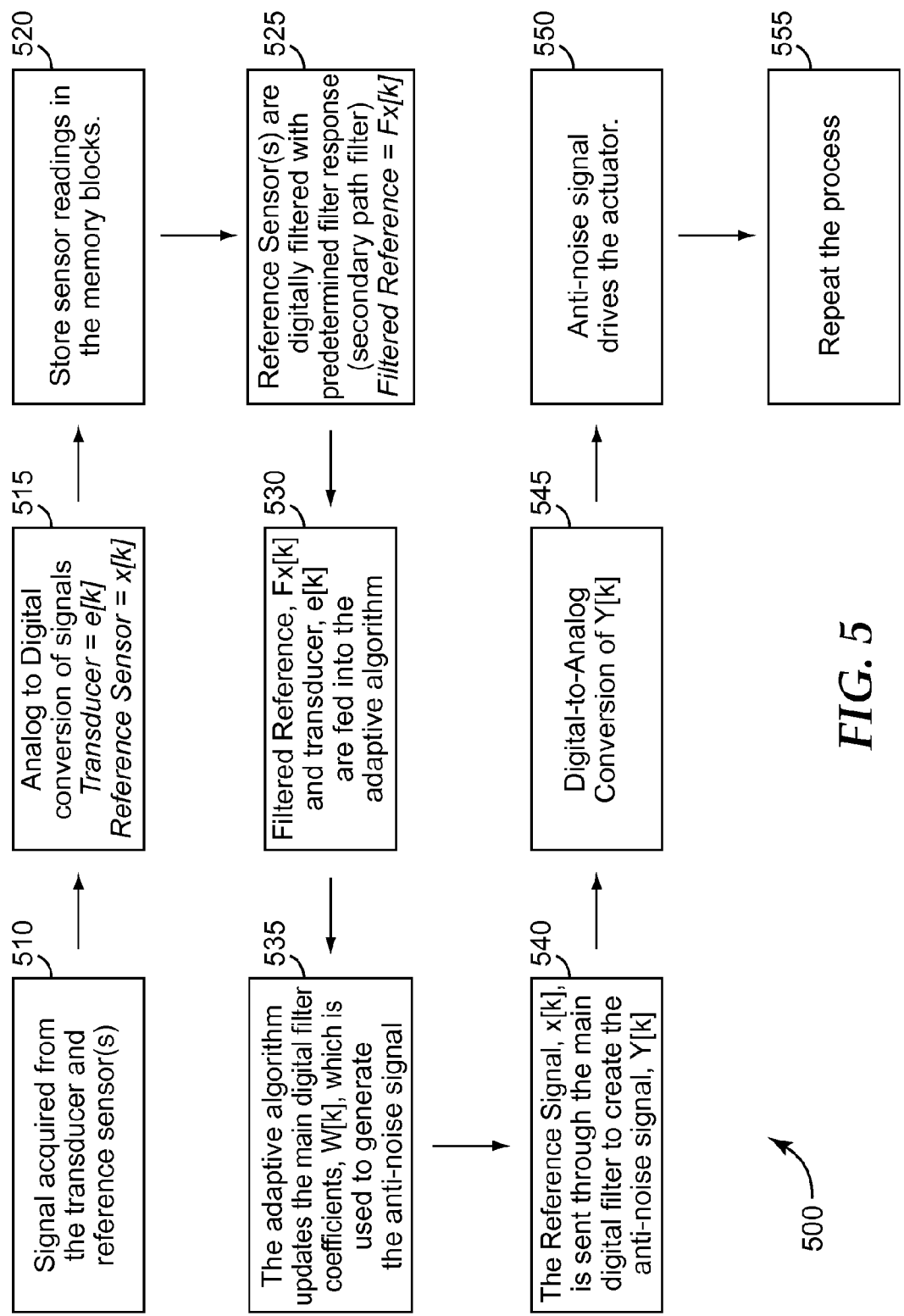
FIG. 5 is a block diagram detailing a method of reducing the effect of a vibration sensed by a transducer according to an implementation of the present disclosure.
Figure 6:
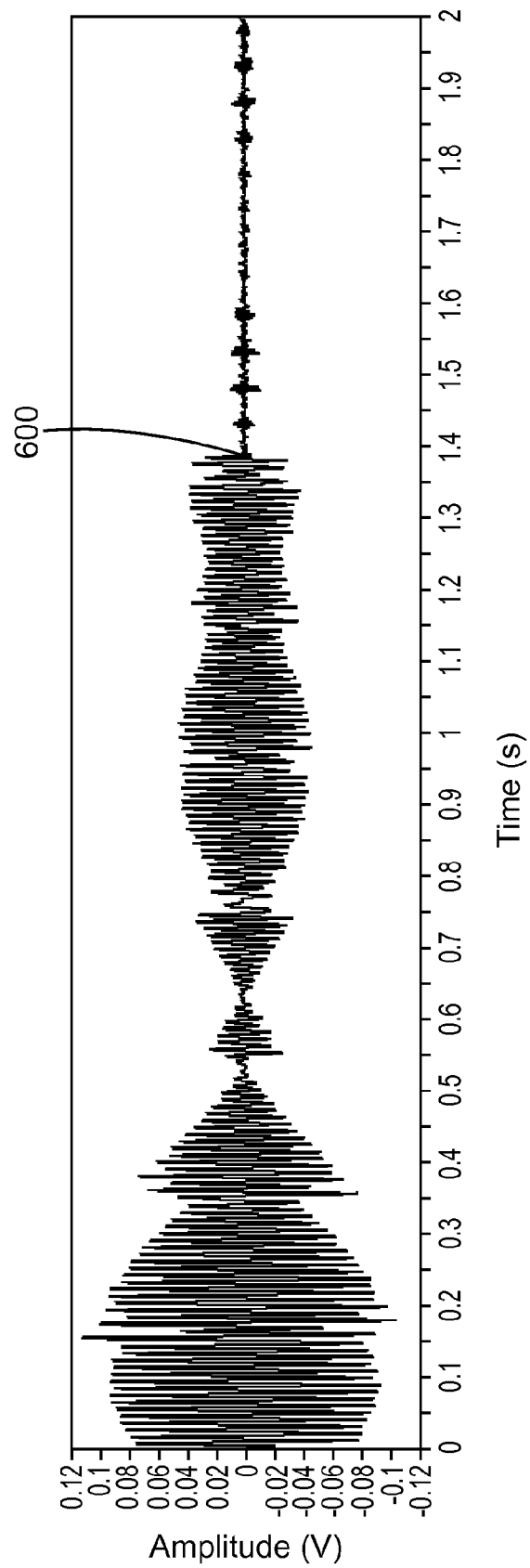
FIG. 6 is a graphical representation of an acoustic signal before and after implementation of a vibration control feedback loop according to the present disclosure.

Referring to the drawings, FIG. 1 illustrates certain components of an exemplary bioacoustic sensor system of the present disclosure. FIGS. 2 and 3 illustrate transducer assemblies particularly suited for use in the sensor systems of the present disclosure. FIG. 4 illustrates an aspect of the noise vibration control circuitry used in generating an actuator control signal. FIG. 5 illustrates a process for improving the signal-to-noise ratio of an acoustic signal using certain vibration countering methods of the present disclosure. FIG. 6 illustrates an exemplary improvement in signal-to-noise ratio using the vibration countering methods of the present disclosure.

As depicted in FIG. 1, a bioacoustic sensor system 100 can include a primary transducer assembly 200 one or more reference sensors 110, a signal processing circuit 300, and an output module 400. The various components of the bioacoustic sensor system 100 can be hosted in a single housing 101 or multiple housings coupled via wired or wireless connection. In the embodiment depicted in FIG. 1, all of the components used to receive and process signals from the primary transducer assembly 200 and reference sensor 110 are housed within the same housing 101. Alternatively, some or all of the components used to receive, process, or receive and process the signals are housed in a separate housing from the primary acoustic sensor 200 and/or reference sensor 110. The reference sensor 110 can be located in the same or different housing than primary transducer assembly 200.

Other components that may be disposed in or on the housing 101 include a power source, a microprocessor, a keypad, a graphical user interface, and a communications module (e.g., a radio). Some or all of these components provided may be remote from the housing. In addition, signal processing circuit 300 may include power management circuitry such as that described in U.S. Patent Application Publication No. 2008/0232604, entitled "Power Management for Medical Sensing Devices Employing Multiple Sensor Signal Feature Detection".

The transducer assembly 200 includes both an actuator 210 and an acoustic transducer element 220. The transducer element 220 is configured to modulate or generate an electric, acoustic signal 120 in response to deformation thereof by impinging acoustic vibrations. The transducer assembly 200 is typically arranged in the housing 101 to be preferentially sensitive to bioacoustic energy transferred via a patient interfacing portion of the housing relative to energy transferred via other portions of the housing. Though preferentially sensitive to sounds emanating from a patient, the acoustic signal 120 generated by deformation of the transducer 220 will typically include both a physiological component and a noise component. The physiological component of the acoustic signal 120 is indicative of a measured physiological parameter, such as sounds generated by a beating heart, respiration, etc. The noise component can be indicative of noise from an external noise source, such as electronics (e.g., computers, medical equipment, motors, pumps, fans, alarms, or other electronics, etc.), noise from others in the vicinity of the patient, vehicle noise (e.g., in a helicopter), and other structure borne vibrations. In some embodiments, the noise component is indicative of acoustic sounds emanating from the patient that are not indicative of measured physiological parameters (e.g., patient speech, coughing, patient movement, etc.).

Similar to transducer element 220, a reference sensor 110 is configured to modulate or generate a reference signal 130 in response to impinging acoustic vibrations. Unlike transducer assembly 200, however, reference sensor 110 is typically arranged in the housing 101 to be preferentially sensitive to ambient noise. As used herein, "ambient noise" means all unwanted noise vibrations potentially sensed at the transducer, including, but not limited to, environmental noise, non-parameter patient sounds, and other sensor structure borne vibrations. In certain circumstances, the vibrations sensed by reference sensor 110 will still include a minor physiological component as well as a noise component. The reference sensor 110 can be located on the exterior or interior of the housing 101 remote from transducer assembly 200. In certain particularly useful implementations, the system 100 includes a plurality of reference sensors 110a, 110b. The selection of a particular reference sensor may be specific to the conditions of the noise environment and the type of acoustic signal being sensed, from which the noise is to be removed. That is, in some embodiments, one or more different types of reference sensors may be used, for example an accelerometer may be the preferred vibration reference sensor rather than an acoustic microphone, while in other circumstances an acoustic microphone may provide a better reference signal to generate the anti-noise signal. In still other circumstances a combination of different reference sensor types may be preferred over the selection of a single reference sensor type. The selection of the type or types of single or multiple reference sensors to be used may be accomplished manually by the device user. The device user may manually select the type and number of reference sensors by pushing a button or via touch screen selections. Alternatively, the selection of single or multiple reference sensors and the type of references sensors may be accomplished automatically by the device through a preliminary noise assessment routine performed automatically by the device. The result of the preliminary noise assessment routine would be that the device automatically selects the number and type of reference sensors appropriate for particular noise environment and type of acoustic sensing being performed.

Suitable transducer elements 220 are those that incorporate piezoelectric material (organic and/or inorganic piezoelectric material) such as piezoelectric film, piezoresistive material, strain gauges, capacitive or inductive elements, a linear variable differential transformer, and other materials or elements that modulate or generate an electrical signal in response to deformation (e.g., certain microphone diaphragms). The transducer element may be planar or non-planar, such as in the case of a curved or corrugated configuration. Suitable piezoelectric materials may include polymer films, polymer foams, ceramic, composite materials or combinations thereof. Lead zirconate titanate (PZT) ceramic is a particularly suitable piezoelectric material. In embodiments wherein the transducer element is or includes a piezoelectric material, deformation of the transducer element 220 changes the relative positions of charges in the polymer chain or in the semi-crystalline lattice structure, thereby producing a voltage having an amplitude related (e.g., proportionally related) to the magnitude of deformation of the sensing element. It is also known that certain semi-crystalline polymers, such as polarized fluoropolymer polyvinylidene fluoride (PVDF), have piezoresponsive properties, which may include piezoelectric response. PVDF is used in various sensors to produce a voltage as a function of force or displacement. Polymer resin piezoelectric materials can be useful because the polymers can be embodied as sensing elements which are both flexible and elastic, and develop a sense signal representing resiliently biased deformation when subjected to force.

The piezoelectric material can comprise one or more conductive layers. The conductive layers can include metallization layers that are adhered to the surfaces of the piezoelectric material. Metallization of the surfaces of the piezoelectric material may be accomplished using any suitable material and any suitable technique known in the art. For example, thin layers of a metal, such as nickel, silver, copper or alloys thereof, can be deposited on the surfaces of a piezoelectric material. In other embodiments, the conductive layers can comprise or be coated with a conducting ink. The conductive layers may comprise the same or different material. The voltage generated on deformation is typically transferred to one of the adjacent conductive layers. In another implementation, the transducer element 220 may comprise a laminate structure. The laminate structure may comprise a piezoelectric film, a weight in film form, and one or more adhesive layers.

The reference sensor 110 can comprise any of the piezoelectric sensors described above. Alternatively, the reference sensor 110 may be implemented using technologies other than those that employ piezoelectric materials. For example, the reference sensor 110 may comprise a microphone disposed on the exterior or interior of housing 101. As a further example, the reference sensor 110 may comprise an accelerometer (e.g., a MEMS accelerometer) coupled to or disposed in the housing and employed to produce electrical or optical signals corresponding to sensed acoustic vibrations.

The acoustic signal 120 and the reference signal 130, typically in analog form, are communicated to signal processing circuitry 300, which is configured to generate a processed signal 350 for communication to an output device 400. The signal processing circuitry 300 can include front end processing componentry 330 configured to condition analog signals for processing. For example, front end processing componentry may comprise preamplifiers, filters (e.g., band pass filter), amplifiers, and/or analog-to-digital converters. In other embodiments, other circuitry may be provided in addition to or instead of these circuit components. The signal processing circuit 300 further includes a vibration control module 310, which is configured to generate a control signal 340 for exciting an actuator 210 to selectively deform transducer 220 of primary transducer assembly 200.

As will be explained in further detail below, the vibration control module 310 is configured to analyze and identify characteristics (e.g., frequency, phase, amplitude) of the noise components in at least the reference signal 130. The vibration control module includes at least one filter (typically digital) and an adaptive algorithm. Similar to some methods of traditional active noise cancellation, the reference signal 130 is passed through a filter, and the output of the filter is subtracted from the acoustic signal 120. The filter includes a time varying transfer function. An adaptive algorithm is used to adapt the filter frequency response, where the algorithm adjusts filter coefficients based on the input from the reference signal 130 and, in certain implementations, the acoustic signal 120. One exemplary adaptive system uses an adaptive finite impulse response (FIR) digital filter, and a gradient based adaptive algorithm (such as a filtered-X LMS algorithm), but many other system configurations are possible.

In addition to filter adaptation, the vibration control module 310 is configured to generate a control signal 340, which is representative of the noise component of the acoustic signal 120. In certain implementations, the control signal 340 is representative of the noise component of the reference signal 130. The characteristics of control signal 340 will be at least partially based on the one or more characteristics (e.g., phase, amplitude, frequency) of the noise component. Once generated, the control signal 340 is fed back to an actuator 210 of the acoustic transducer assembly 200.

The actuator 210 is physically coupled to at least a portion of the transducer element 220. The actuator 210 is configured to deform a portion of the transducer 220 in response to the control signal 340. Typically, the actuator 210 is configured to deform the transducer 220 via transfer of energy to a surface of the transducer 220. The extent of energy transferred, and accordingly deformation, corresponds at least partially to one or more characteristics of the noise component of acoustic signal 120 and/or reference signal 130. For example, the greater the amplitude of the noise component of acoustic signal 120, the greater the deformation necessary to offset the vibrations related to that noise sensed at transducer 220. In such circumstances, the actuator 210 will transfer more energy to the transducer 220 to counteract vibrations than in other, quieter circumstances. In particularly useful aspects, the actuator 210 comprises a piezoelectric transducer. Alternatively, the actuator 210 can include linear solenoids, piston, and other known actuators In some implementations, the signal processing circuit can utilize other downstream noise reduction techniques in a noise control module. Such traditional noise control modules may, for example, combine (e.g., sum, subtract, average, etc.) the reference signal(s) 130 and the acoustic signal 120 in a manner that tends to reinforce the physiological signal components of the acoustic signal 120 while tending to cancel or reduce the noise components of the acoustic signal 120. Such techniques may operate to lower the ambient acoustical noise level and/or provide the bioacoustic sensor system with improved noise immunity. For example, the traditional noise control module can include a noise attenuator which performs the combining of the signals from one or more reference sensors to achieve an improved signal-to-noise ratio. Suitable noise reduction or cancellation techniques include adaptive and static active noise control, anti-noise signal generation for receipt at an output device, and digital filtering to remove noise components. Exemplary downstream noise reduction techniques may be found in U.S. Pat. No. 5,539,831 (Harley), U.S. Pat. No. 5,812,678 (Scalise et al.), U.S. Pat. No. 6,028,942 (Greenberger) U.S. Pat. No. 8,024,974 (Bharti et al.) and US Publication No. 2011/0125060 (Telfort et al.).

The signal processing circuit 300 may be configured to perform a variety of additional functions, ranging from simple to complex. For example, the signal processing circuitry 300 may be configured to perform relatively sophisticated analysis of bioacoustic signals received from the transducer assembly 200, such as body sound profile matching. The signal processing circuitry may perform various forms of statistical analysis on signals produced by the transducer assembly 200. In such configurations, the signal processing circuitry may include a digital signal processor (DSP). As a further example, the signal processing circuitry may perform selective frequency filtering to enhance different types of body sounds sensed by transducer assembly 200. In some embodiments, the bioacoustic sensor system is an electronic stethoscope configured to generate acoustic signals as described in U.S. Pat. No. 6,134,331, entitled "Electronic Stethoscope," U.S. Pat. No. 7,006,638, entitled "Electronic Stethoscope," U.S. Pat. No. 7,130,429, entitled "Method and an Apparatus for Processing Auscultation Signals," U.S. Pat. No. 8,024,974, entitled "Cantilevered Bioacoustic Sensor and Method of Using Same" and/or Application No. 61/568,411, entitled "Electronic Stethoscopes with User Selectable Digital Filters".

In some embodiments, a digital filter or a separate processing unit (not shown in FIG. 1) may process the filtered signals to provide various output data, such as a visual, graphical and/or audible representation of the information (e.g., heart rate indication, S1-S4 heart sounds), and/or diagnostic information regarding anomalous cardiac, lung, or other organ function (e.g., phonocardiogram, frequency spectrogram, cardiac murmurs such as those resulting from valve regurgitation or stenosis, breathing disorders such pneumonia or pulmonary edema), or other organ pathology. In some implementations, the separate processing unit or digital filter may reside on the output device 400.

The signal processing circuit 300 can optionally include a communication module to communicate processed signal 350 by wired and/or wireless connection. The wired connection may be via interfaces of a variety of protocols, for example, Universal Serial Bus (USB), Mini USB, FireWire™ (IEEE 1394 Interface), Internet, or other communication protocol. In addition, the communication module may be configured to connect to a docking station that interfaces with a computing device. When connected, recharging power may also be delivered to the bioacoustic sensor system 100 via a wired connection port. The attachment of the bioacoustic sensor system 100 to the cable or docking station can trigger the automatic launch of control/application software on the computing device and/or allow sound or data files stored on the bioacoustic sensor system to upload or synchronize into the computing device. In some implementations, the computing device can be the output device 400.

The communication module can support a wireless connection with any short-range or long range wireless interfaces. The short-range communication interfaces may be, for example, interfaces conforming to a known communications standard, such as Bluetooth standard, IEEE 802 standards (e.g., IEEE 802.11), a ZigBee or similar specification, such as those based on the IEEE 802.15.4 standard, or other public or proprietary wireless protocol. The long-range communication interfaces may be, for example, cellular network interfaces, satellite communication interfaces, or the like. The communication module may utilize a secured communication link.

Output device 400 can be any device suitable for receiving and/or reproducing acoustic signals for user consumption. Suitable output devices 400 include, but are not limited to, headsets, computing devices, mobile devices (for example, cellular phones, smart-phones, personal digital assistants (PDA), and tablets), personal computers (PC), and the like. In certain embodiments, some or the entire signal processing circuitry 300 may reside as hardware or software on the output device 400. For example, the housing 101 may include front end processing componentry 330 and a communication module. The output device 400 may include vibration control module 310 and thus be configured to generate control 340 for eventual communication to actuator 210.

Output device 400 can include a consumer-style headset linked by analog/digital cables or by a wireless link (e.g., Bluetooth). The headsets may be equipped with additional active noise cancellation circuits or anti-noise signal generators/speakers. These may be of a general design not limited to traditional medical applications. Military-style headset modules may be linked to an output module 400 by analog/digital cables or by a wireless link. Military-style headsets may be embedded in a protective helmet and be capable of operating in extreme environments. The particular nature of the link and output device circuitry may be based on military communications standards.

Referring now to FIG. 2, a transducer assembly 200 is shown disposed in housing 101. The transducer assembly 200 is shown in cross-section and includes an acoustic transducer element 220, an actuator 210, an insulating layer 230, a compliant anchoring arrangement 240, a compliant ring 250, and a rigid disc 260. The assembly 200 may be coupled to the housing via fixation mechanism 270. The transducer assembly 200 can be contained in a separable transducer housing 201 within a cavity of the main housing 101. Transducer housing 201 is typically comprised of a rigid material, e.g., stainless steel, aluminum, other metals and or metal alloys, or rigid polymers and can potentially shield the transducer assembly from some unwanted acoustic vibrations (i.e., noise).

The housing 101 typically includes an interfacing portion 105 configured to establish coupling with a body part during use of the sensor system 100. For example, the interfacing portion 105 may be the surface of the housing 101 (e.g., a diaphragm cover) that comes into contact with a patient's chest or clothing covering the chest. The interfacing portion 105 is preferably formed from, or incorporates, material that facilitates transmission of vibrations from the interfacing portion 105 to the transducer 220, such vibrations resulting from bioacoustic energy emanating from the body and impinging on the housing 101. The housing 101 can also include a non-interfacing portion, which may be a region of the housing 101 that faces the ambient environment during use of the sensor system 100. The non-interfacing portion, which may be a separable cover, may incorporate acoustically absorptive material or other vibration attenuation material or arrangement.

The transducer assembly 200 is mounted within the housing 101 so that the transducer element 220 is preferentially sensitive to bioacoustic energy transmitted via the interfacing portion 105 relative to other portions of the housing 101. In the configuration shown in FIG. 2, for example, transducer 220 has two opposing major surfaces 221, 222. The transducer assembly 200 is mounted within the housing 101 so that the major surfaces 221, 222 of the transducer 220 are substantially parallel to the interfacing portion 105 of the housing 101. Other orientations are possible depending on the particular transducer and housing features and characteristics.

As depicted in FIG. 2, actuator 210 is disposed above (relative to the interfacing portion) and is coextensive with the transducer 220. In other implementations the actuator 210 extends over only a portion of the first major surface 221 of the transducer 220, so long as the actuator 210 remains capable of deforming an effective transducing portion thereof. In certain aspects, it can be acceptable for the actuator 210 to be disposed directly on the surface 221 of transducer 220. In other implementations, it may be desirable to include additional layers of material between the actuator 210 and the transducer surface 221.

The actuator 210 can be directly physically coupled to transducer 220 via a bonding layer 230. The bonding layer 230 can be a continuous coating, a patterned coating, or discrete portions of bonding material, or combinations thereof. The bonding layer 230 can include epoxy adhesive, spot-weld, or other known fastening mechanism. In particularly useful aspects, the bonding layer 230 is an electrically insulating material that prevents the transmission of electrical charge between the transducer element 220 and the actuator 210. Such insulation can be particularly desirable in assembly implementations featuring a piezoelectric transducer and a piezoelectric actuator. For example, an adhesive such as a double sided 3M™ VHB™ tape, available from 3M Company, can be utilized as insulating material. Additional, suitable insulating materials include Scotch™467MP Hi Performance tape, also available from 3M Company, St. Paul, Minn.

If insulated from the transducer 220 by bonding layer 230, the actuator 210 can also be piezoelectric transducer. In such implementations, the actuator 210 may have the same or different polarity as the transducer 220. The bonding layer 230 can accordingly prevent an electrical short when both transducer 220 and actuator 210 are exposed to acoustic vibrations. In certain particularly useful aspects, the actuator 210 and the transducer 220 can include the same piezoelectric material. An exemplary suitable piezoelectric material for both the actuator 210 and transducer 220 is a piezoceramic sensor available from YEC Electronics, Taiwan.

A compliant anchoring arrangement 240 can be coupled to the second major surface 222 of transducer 220. A similar, compliant ring 250 surrounds a periphery of a surface of the actuator 210. The anchoring arrangement 240 and conformable ring 250 preferably comprise a foam material. Suitable foams include cellulose foams, glass foams, ceramic foams, polymeric foams, and combinations thereof. Suitable closed cell foams include polyolefin foams, particularly polyethylene foams, such as those available from Sekisui Voltek, Lawrence, Mass. The anchoring arrangement 240 can be coextensive with transducer 220, while the conformable ring typically does not extend across the entire outer surface of the actuator 210. Without wishing to be bound by theory, the compliant anchoring arrangement 240 allows transducer 220 to deform according to external vibrations, while preventing the actuator 210 and transducer 220 from acting in concert as a separate system.

The surface of the anchoring arrangement 240 facing the interfacing portion 105 is secured to a rigid disc 260. The rigid disc 260 preferably comprises a metal or alloy. The rigid disc 260 can potentially protect the transducer 220, and other components of transducer assembly 200, from punctures or other undesirable energy transfers. The disc 260, and thus the transducer assembly 200, may be secured to interfacing portion using a rigid or compliant fixation arrangement 270, such as an epoxy, a chemical bond, a weld or solder joint, a screw(s)/nut(s), rivet(s) or other mechanical coupling, or pressure sensitive adhesive, for example. A suitable fixation arrangement 270 may include No. 924 Scotch Adhesive Transfer Tape or No. DP100 Scotch Weld epoxy adhesive, both available from 3M, St. Paul, Minn.

FIG. 3 depicts a diagram of a transducer assembly 200a according to another implementation of the present disclosure. The transducer assembly 200a includes a transducer 220a, an actuator 210a, a bonding layer 230a, a compliant anchoring arrangement 240a, a compliant ring 250a, and a rigid disc 260a. The assembly 200a may be coupled to a housing 101a via fixation mechanism 270a. Elements not specifically discussed below are the same as or substantially similar to those in FIG. 2 and will not be discussed in detail with respect to FIG. 3.

The actuator 210a extends over only a portion of the major surface 221a of the transducer 220a. As depicted, no portion of the actuator 210a extends to the periphery of the transducer 220a. In certain implementations, both the actuator 210a and the transducer 220a are disc shaped or circular, and the actuator 210a is concentric with the transducer 220a. Accordingly, portions of the transducer surface 221a are exposed to the interior of housing chamber 106a. The housing 101a can include openings 107a, 108a to the exterior environment. The openings 107a, 108a allow ambient noise into the interior chamber 106a. This ambient noise impinging on the major surface 221a of the transducer will typically arrive out of phase with the same ambient noise vibrations impinging on major surface 222a arriving from the proximate the patient's body and through fixation mechanism 270a, rigid disc 260a, and compliant anchoring arrangement 240a. By summing the out of phase noise components sensed, those noise components are essentially canceled from the acoustic signal. Further discussion of the effect of ambient noise received at opposing surface 221a can be found in, for example, U.S. Pat. No. 7,593,534 (Andersen).

Turning now to FIG. 4, an embodiment of a signal processing circuit 300 for processing analog signals from a plurality of acoustic sensors is depicted. Input signals are provided, like bioacoustic sensor system 100, by transducer assembly 200 and one or more reference sensors 110. The transducer assembly 200 and reference sensor 110 are configured to generate analog acoustic signal 120 and analog reference signal 130, respectively, in response to sensed acoustic vibrations. As discussed above, the acoustic signal 120 includes both a physiological component and an ambient noise component. The reference signal 130 consists primarily of an ambient noise component, but may include minor physiological components as well. In either scenario, the reference signal 130 is primarily representative of ambient noise. In certain embodiments, the acoustic signal 120 and reference signal 130 are generated simultaneously or near-simultaneously.

The acoustic signal 120 and the reference signal 130 can be communicated to signal processing circuitry 300 in separate signal paths. The signal processing circuitry 300 includes front end processing componentry 330 configured to condition analog signals for further processing. In the embodiment depicted in FIG. 4, the front end componentry includes at least analog-to-digital (A/D) converters 331, 333 and memory 332, 334. The A/D converters 331, 333 may be provided as distinct circuit components or as single entity with multiple, dedicated channels. Once converted, the digital acoustic signal and digital reference signal are communicated to memory 332, 334. If multiple reference sensors are used, each additional reference signal can include its own dedicated converter and memory. The signals 120, 130 are sampled by memory blocks 332, 334 for a predetermined length of time before an averaged signal is the communicated to vibration control module 310. The averaged acoustic signal may be represented by e[k] and the averaged reference signal as x[k].

The vibration control module 310 includes a reference filter 311, an adaptive algorithm module 313, a primary digital filter 315, and a digital-to-analog converter 317. The one or more reference signals, x[k], are provided to the reference filter 311. The reference signal fitter 311 can be configured to account for propagation and/or processing delay differences between the reference signal and the acoustic signal, or between multiple reference signals. In embodiments wherein both the reference sensor and the transducer assembly comprise a transducer, the reference filter 311 can include a mixer to account for differences in vibration propagation path and/or processing delay. As another example, in embodiments featuring a reference sensor that is not a transducer, the reference signal filter can compensate for the differences in transfer function between reference sensor and the transducer. The transfer function of both the reference sensor(s) 110 and the transducer 220 may be selected or determined prior to use. Methods for determining the transfer function of a sensor are known and include those described in Application No. 61/568,411, entitled "Electronic Stethoscopes with User Selectable Digital Filters" and U.S. Pat. No. 5,539,831 (Harley). The determined difference between the transfer functions may be subtracted from the reference signal. The reference filter 311 generates a filtered reference signal, represented as Fx[k].

The filtered reference signal Fx[k] and acoustic signal e[k] are provided to an adaptive algorithm module 313. In preferred embodiments, the adaptive algorithm 313 and digital filter 315 comprise a filtered-X Least Mean Square (FXLMS) algorithm. The adaptive algorithm 313 is used to adapt the response of primary digital filter 315, where the algorithm adjusts filter 315 coefficients based on the input from the filtered reference signal Fx[k], and in certain implementations, the acoustic signal.

At each iteration, the adaptive algorithm module attempts to minimize the noise power in the acoustic signal e[k] by adjusting the coefficients of the digital filter 315. The reference signal x[k] is communicated through the adjusted digital filter 315 to generate the vibration control signal, which can be represented by Y[k]. This vibration control signal is representative of the noise component of the acoustic signal 120 and therefore the characteristics of the vibration control signal Y[k] will be at least partially based on the one or more characteristics (e.g., phase, amplitude, frequency) of the noise component.

The anti-noise control signal Y[k] is fed back to an actuator 210 of the acoustic transducer assembly 200. The anti-noise vibration control signal may be converted from digital to analog and amplified by converter module 317 prior to being provided to the actuator. Since the control signal Y[k] is primarily representative of noise components, the extent of deformation of the transducer by the actuator will be directly proportional to the amount of periodic noise in the original signal.

Turning now to FIG. 5, a method 500 for improving the signal-to-noise ratio of an acoustic transducer is described. The method may be implemented using any of the bioacoustic sensor systems and system components described above. In block 510, an acoustic signal representative of measured physiological parameters and ambient noise is generated by a primary acoustic transducer. Simultaneously, or near simultaneous, a reference signal primarily representative of ambient noise is generated by an acoustic reference sensor. In certain preferred embodiments, multiple reference signals are generated by multiple reference sensors. Both the acoustic signal and reference signal can be converted from analog to digital signals, as represented in block 515. This conversion generates an acoustic signal represented by e[k] and at least one reference signal represented by x[k]. In block 520, the acoustic signal e[k] and the reference signal x[k] are sampled over a predetermined length of time for storage in memory. In other implementations, only the reference signal x[k] is stored/sampled. Once a desired amount of sampling of the reference signal x[k] has occurred, the reference signal(s) x[k] is filtered to compensate for propagation path differences and the like in block 525 The filtered (compensated) reference signal Fx[k], as well as the acoustic signal e[k], are provided to an adaptive algorithm, which identifies and predicts the noise components of the respective signals in block 530. Having the identified the noise components in block 530, the adaptive algorithm communicates with a digital filter to change the filter coefficients in block 535, thereby modifying the transfer function of the digital filter. In block 540, newly acquired or stored reference signals x[k] are provided to the newly adapted digital filter, which filters the components of reference signal to generate anti-noise vibration control signal Y[k]. The digital anti-noise vibration control signal Y[k] may be converted to an analog signal and/or amplified (block 545). The anti-noise vibration control signal Y[k] then causes the actuator to deform the transducer, according to characteristics of the noise components in block 550. Typically, deforming the transducer comprises transferring mechanical energy via the actuator to at least a portion of a surface of the transducer. That surface is generally opposite the surface of the transducer nearest to the patient. The magnitude of the energy is determined by at least one characteristic of a component of the reference signal and at least one characteristic of a component of the acoustic signal. The deformation of the transducer by the actuator may continue so long as noise components are sensed by the transducer and/or reference sensors, and attendant anti-noise vibration control signals are generated (block 555).

As illustrated by FIG. 6, the signal-to-noise ratio of the acoustic signal can be substantially improved by operation of the vibration control module and the actuator. The acoustic signal depicted in FIG. 6 initially includes a substantial noise component with high amplitude, with frequency content of 60-80 Hr. At time 600, the vibration control module is engaged and the amplitude of the noise is significantly reduced. In some implementations, the signal-to-noise ratio can be improved by at least 20 dB, in some embodiments at least 15 dB, and in some embodiments at least 10 dB, and in yet other embodiments improved by at least 5 dB.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A system for acquiring bioacoustic signals, the system comprising:
   a transducer assembly including a transducer configured to sense a manifestation of acoustic energy and an actuator physically coupled to a major surface of the transducer, wherein the transducer is configured to generate an acoustic signal;
   a reference sensor configured to generate a reference signal;
   a processor coupled to the reference sensor and the transducer; and
   noise vibration control circuitry coupled to the reference sensor and the actuator, the noise vibration control circuitry configured to generate an anti-noise signal based at least partially on a component of the reference signal, the anti-noise signal operable to cause the actuator to deform at least a portion of the transducer, wherein the deformation of the transducer increases a signal-to-noise ratio of the acoustic signal.

2. The system of claim 1, wherein the transducer is coupled to the actuator by an electrically insulating material.

3. The system of claim 1, wherein at least one of the transducer and the actuator comprises a piezoelectric material.

4. The system of claim 1, wherein the references signal comprises a component representative of noise, the noise comprising at least one of environmental and structure borne noise.

5. The system of claim 1, wherein the actuator is operable to deform the transducer by applying mechanical energy to at least a portion of the first major surface of the transducer.

6. The system of claim 1, wherein the deformation of the transducer comprises reducing at least a portion of a vibration sensed at the transducer, the portion of vibration being reduced indicative of unwanted noise and wherein the extent of deformation corresponds at least partially to a component of the reference signal.

7. A bioacoustic sensor comprising:
   a housing configured for hand-held manipulation;
   a transducer assembly supported by the housing that senses auscultation signals, the transducer assembly comprising a transducer having a first major surface and an actuator physically coupled to the transducer;
   a headset coupled to the housing and configured to deliver audio corresponding to the auscultation signals through earpieces on the headset;
   a reference sensor configured to generate a reference signal;
   a processor disposed in the housing and configured to convert the auscultation signals to first digital signals representative of the auscultation signals; and
   noise vibration control circuitry coupled to the reference sensor and the actuator, the noise vibration control circuitry configured to generate an anti-noise signal, wherein the anti-noise signal is based at least partially on a component of the reference signal and is operable to cause the actuator to deform at least a portion of the transducer, and wherein the deformation of the transducer increases a signal-to-noise ratio of the acoustic signal.

8. The bioacoustic sensor of claim 7, wherein the transducer assembly further comprises an electrical insulating material disposed between the transducer and the actuator.

9. The bioacoustic sensor of claim 8, wherein the transducer and the actuator comprise piezoelectric material.

10. The bioacoustic sensor of claim 7, wherein the housing comprises a chamber having an opening to the exterior environment so that ambient noise may enter the chamber, wherein the housing comprises an interfacing portion configured to establish coupling with a body part during use and an inner surface opposite the interfacing portion, wherein a second major surface of the transducer is coupled to the inner surface of the housing, wherein the actuator is coupled to the first major surface opposite the second major surface of the transducer and wherein the actuator does not extend to the periphery of the transducer.

11. A method of increasing the signal-to-noise ratio of a signal generated by an acoustic sensor, the method comprising:
   providing a transducer assembly and a reference sensor remote from the assembly, wherein the transducer assembly comprises a transducer and an actuator coupled to a major surface of the transducer;
   providing noise vibration control circuitry coupled to the reference sensor and the actuator;
   generating an acoustic signal from the transducer and a reference signal from the reference sensor;
   providing at least the reference signal to the noise vibration control circuitry;
   generating an anti-noise signal based at least partially on a component of the reference signal;
   providing the anti-noise signal to the actuator; and
   deforming at least a portion of the transducer via the actuator.

12. The method of claim 11, wherein deforming the transducer comprises transferring mechanical energy via the actuator to at least a portion of the major surface of the transducer.

13. The method of claim 12, wherein the magnitude of the energy is determined at least partially by at least one characteristic of a component of the reference signal.

14. The method of claim 11, wherein generating an anti-noise signal comprises filtering the reference signal and the acoustic signal through an adaptive filter.

* * * * *